United States Patent [19]
Avakian et al.

[11] Patent Number: 5,196,514
[45] Date of Patent: Mar. 23, 1993

[54] METHOD OF DETECTING MYCOPLASMA INFECTION IN POULTRY AND COMPOSITIONS THEREFOR

[75] Inventors: Alan P. Avakian, Raleigh, N.C.; Stanley H. Kleven, Athens, Ga.

[73] Assignee: The University of Georgia Research Foundation, Inc., Athens, Ga.

[21] Appl. No.: 489,011

[22] Filed: Mar. 6, 1990

[51] Int. Cl.$^5$ .................... C12N 1/00; C12N 1/20; C07K 3/00; C07K 13/00; C07K 15/00; C07K 17/00
[52] U.S. Cl. .................................. 530/350; 435/863
[58] Field of Search ................ 530/350, 403; 435/863

[56] References Cited

PUBLICATIONS

Opitz et al (1983) Avian Disease 27:773–786.
Bradley et al (1988) Am J Vet Res 49:511–515.
Talkington et al (1985) Avian Dis. 29:53–71.
Yogev, D. et al., Veterinary Microbiology, 19:75–84 (1989).
Kleven, S. H. et al., Avian Diseases, 32:731–741 (1988).
Thomas, C. B. et al., Avian Diseases, 32:748–756 (1988).
Ahmad, I. et al., Avian Diseases, 32:519–526 (1988).
Bradbury, J. et al., Israel J. Med. Sci., 23:771–772 (1987).
Yoder, H. W. et al., Avian Diseases, 30:510–518 (1986).
Opitz, H. M. et al., Avian Diseases, 30:213–215 (1986).
Patten, B. E. et al., Australian Vet. J. 61:151–155 (1984).
Glisson, J. R. et al., Avian Diseases, 28:397–405 (1984).
Mallinson, E. T., Avian Diseases, 27:330–331 (1983).
Ansari, A. A. et al., Avian Diseases, 27:21–35 (1983).
Jordan, F. T. W., The Mycoplasmas, 2:1–48 (1979).
Kleven, S. H., Am. J. Vet. Res., 36:563–565 (1975).
Bradbury, J. M. et al., The Veterinary Record, pp. 591–592 (Jun. 2, 1973).
Cullen, G. A. et al., British Veterinary Journal, 128:94–100 (1972).
Bradbury, J. M. et al., J. Hygiene, 70:267–278 (1972).
Bradbury, J. M. et al., The Veterinary Record, p. 318 (Sep. 11, 1971).
Roberts, D. H., The Veterinary Record, 87:125–126 (1970).
Vardaman, T. H. et al., Poultry Science, 49:157–160 (1970).
Roberts, D. H., J. Applied Bacteriology, 32:395–401 (1969).
Roberts, D. H. et al., Avian Diseases, 11:104–119 (1967).
Olson, N. O. et al., Am. J. Vet. Res., 26:195–198 (1965).

Primary Examiner—Christine M. Nucker
Assistant Examiner—D. R. Preston
Attorney, Agent, or Firm—Needle & Rosenberg

[57] ABSTRACT

The present invention relates to the identification and purification of antigens from M. gallisepticum and M. synoviae and their use in serological assays. Cell proteins from these organisms that possess substantial immunoreactive responses with poultry antisera to the mycoplasma from which they are isolated in both the acute and convalescent stages of infection are identified. Of these immunogenic proteins, those that also lack immunogenic cross-reactivity with antisera to other poultry mycoplasmas and pathogens are identified. These species specific proteins are purified and incorporated into enzyme-linked immunosorbent assays (ELISAs). The resulting assays are able to detect sensitively and selectively both field or experimentally-induced M. gallisepticum or M. synoviae infection in poultry. A combination of these assays are incorporated into a diagnostic kit to allow the rapid, sensitive, and selective testing for and differentiation between M. gallisepticum and M. synoviae. This invention also provides anti-serum to these mycoplasma antigens and an immunoassay that employs this anti-serum to detect infection in poultry. Furthermore, a method to produce genetic clones that express the antigenic portions of the mycoplasma antigens is provided.

1 Claim, 4 Drawing Sheets

METHOD OF DETECTING MYCOPLASMA INFECTION IN POULTRY AND COMPOSITIONS THEREFOR

ACKNOWLEDGEMENT

The invention described herein was made in part in the course of or under the Binational Agricultural Research and Development Project No. I-939-85 sponsored by the Governments of the United States and Israel.

BACKGROUND OF THE INVENTION

The present invention relates to compositions and methods for detecting mycoplasma infection in the commercial poultry industry. More particularly, the invention relates to the identification and purification of antigens and antisera that are capable of detecting and distinguishing infection caused by *Mycoplasma gallisepticum* and *Mycoplasma synoviae* and the use of these antigens in serological assays. Furthermore, a method of producing clones which express the antigenic portions of the antigens is provided.

The p64, p56, p26, p41, and p22 antigens described herein have been deposited with the American Type Culture Collection (ATCC) at 12301 Parklawn Drive, Rockville, Md. 20852 U.S.A. under ATCC designation Nos. ATCC 40749, ATCC 40748, ATCC 40746, ATCC 40747 and ATCC 40745, respectively. The deposits will be maintained for a period of thirty years, for five years after the last request for the antigen, or for the enforceable life of the U.S. Patent, whichever is longer. Should the deposits become non-viable, they will be replaced by Applicants. Assurance of access to the deposits as determined by the Commissioner under 37 CFR §1.14 is provided for. All restrictions on the availability of the deposits to the public will be irrevocably removed upon the granting of a patent.

*Mycoplasma gallisepticum*, which can cause respiratory disease in chickens, turkeys, and other species of birds, is one of the most important pathogens affecting the poultry industry. Chickens and turkeys infected with *M. gallisepticum* show a wide variety of clinical signs ranging from asymptomatic to chronic respiratory disease. Common symptoms include rales, nasal discharge, coughing, reduced feed intake, weight loss, and decline in egg production. Airsacculitis in chickens and turkeys related directly or indirectly to *M. gallisepticum* infection is a significant cause of condemnations of carcasses at the processing plant. If breeding stock are infected with *M. gallisepticum*, the typical action is depopulation to prevent egg transmission to the progeny.

*Mycoplasma synoviae* infection in aves causes less debilitating symptoms than *M. gallisepticum* infection. Clinical manifestation of the disease often does not occur. However, lameness with or without generalized disease and respiratory symptoms can reduce optimal production, increase food conversion rates, and cause downgrading of carcasses at the processing plant. Breeder flocks infected with *M. synoviae* might be eradicated.

Poultry breeders and producers need to maintain their flocks free of pathogenic mycoplasmas, particularly *M. gallisepticum*. Because the infection of poultry with either *M. gallisepticum* or *M. synoviae* is often subclinical, screening for signs of infection by these mycoplasmas is usually done by serology. Optimally, this screening process should detect infection in its early stages. The serological test should be sensitive and specific, and identify which mycoplasma species is causing the infection without giving rise to false positive results.

Presently, flocks are screened for antibodies to *M. gallisepticum* or *M. synoviae* by the serum plate agglutination (SPA) test. The SPA test primarily measures IgM and is able to detect antibody in the serum within a week of infection. Unfortunately, the SPA test is prone to false positive results (Boyer et al., *Avian Dis.*, 4:546-547 (1960); Bradbury et al., *J. Hyg.*, 70:267-278 (1971); Avakian et al. *Avian Dis.*, 32:262-272 (1988).

One cause of false positive reactions in the SPA tests, as well as in enzyme-linked immunosorbent assays (ELISA's), stems from the antigenic relationship between *M. gallisepticum* and *M. synoviae;* some of the antigens of *M. gallisepticum* and *M. synoviae* share common epitopes as shown by immunoblotting. In addition to these cross-reactions, strong and frequent positive SPA and ELISA reactions occur when testing chicken antisera to Frey's medium with 12% swine serum (FMS); this result suggests that reactions to medium components contribute to false positive SPA and ELISA serology. Because birds in the field, especially breeders, often receive numerous oil-emulsion vaccines, they are likely to be simultaneously immunized with medium components that were incorporated into the vaccine along with the pathogenic agent. Thus, antisera from poultry often have antibodies directed towards medium components that are likely to cause false positive SPA and ELISA reactions.

Positive SPA test results usually are confirmed by the hemagglutination-inhibition (HI) test, which primarily measures IgG. The HI test, although specific, lacks sensitivity and seldom detects antibody in the serum until two to three weeks after the initiation of infection (Kleven, *J. Vet. Res.*, 36:563-564 (1975); Kleven et al., *Avian Dis.*, 32:731-741 (1988)). Also, the typical *M. gallisepticum* antigen strains used to make HI antigen may not be antigenically similar enough to detect antibodies to some of the atypical *M. gallisepticum* strains.

Enzyme-linked immunosorbent assays (ELISA's) have been developed for *M. gallisepticum* and for *M. synoviae*. However, these ELISA tests suffer from poor sensitivity and/or specificity and are prone to false positive reactions.

Thus, the conventional system used to serodiagnose mycoplasma infections in poultry is less than adequate. These various serological tests are often combined with tracheal culturing to produce a final diagnosis. However, it is often difficult to isolate *M. gallisepticum* and *M. synoviae* in cultures from flocks that are concurrently infected with one or more nonpathogenic mycoplasma species such a *M. gallinarum*, *M. gallinaceum*, *M. pullorum*, *M. gallopavonis,* or *Acholeolasma laidlawii.* These nonpathogenic species usually overgrow the slower growing pathogenic species in vitro. In rare cases, *M. gallisepticum* isolates have taken as long as three weeks to show signs of growth in broth medium. Once isolated, mycoplasmas are identified by a fluorescent antibody technique. These fluorescent antibody reagents are not available commercially; therefore, laboratory personnel must prepare these reagents themselves.

Using these procedures, it takes one to three weeks for experienced laboratory diagnosticians to determine which, if any, species of Mycoplasma are infecting a flock. However, a breeder company can experience significant economic loss each day that *M. gallisepticum* infection in a breeder flock is suspected but unconfirmed. Therefore, there exists a need for reliable, sensitive, and specific serodiagnostic tests that can rapidly detect and differentiate between *M. gallisepticum* and *M. synoviae* infection.

SUMMARY OF THE INVENTION

The present invention relates to the identification and purification of antigens from *M. gallisecticum* and *M. synoviae* and their use in serological assays. Cellular antigens from these organisms that elicit a substantial immunogenic response in poultry in both the acute and convalescent stages of infection are identified. Of these immunogenic antigens, those that also lack immunogenic cross-reactivity or very weak immunogenic cross-reactivity with antisera to other poultry mycoplasmas and pathogens are identified. These antigens are purified and incorporated into ELISAs or other immunoassays. The resulting assays are able to detect sensitively and selectively both field or laboratory-induced *M. gallisepticum* or *M. synoviae* infection in poultry. A combination of these assays are combined into a diagnostic kit to allow the rapid, sensitive, and selective testing for and differentiation between *M. gallisepticum* and *M. synoviae*. Furthermore, a method to produce genetic clones that express the antigenic portions of the antigens is provided.

More specifically, proteins from a particular *M. gallisepticum* or *M. synoviae* strain or isolate were solubilized in a detergent solution, heated to 100° C. with a lysis buffer under reducing conditions, and separated into protein bands using sodium dodecyl sulfate-polyacrylamide gel electrophoresis. Western immunoblots of these protein bands were developed to obtain the relative molecular weights of these protein bands and to test their immunoreactivity with antisera to various pathogenic and nonpathogenic poultry bacteria acquired during various stages of infection.

Four immunogenic protein bands (p64, p56, p26, and p24) isolated from *M. gallisepticum* and three immunogenic protein bands (p53, p41, and p22) isolated from *M. synoviae* were selected as good candidates for further testing as ELISA antigens. These proteins were chosen based on the following criteria: (1) presence of immunogenicity in both the acute and convalescent stages of the infection; (2) representation of a relatively large percentage of the total protein from the mycoplasma cell; (3) lack of cross-reactivity with antisera to other pathogenic and nonpathogenic poultry bacteria; and (4) presence of the protein band in all tested isolates of the mycoplasma species from which they were purified.

Purified samples of these seven protein bands were obtained as follows. Solubilized and boiled total protein preparations from a mycoplasma strain or isolate were separated by SDS-PAGE electrophoresis followed by staining of the proteins to identify the particular antigen band of interest. Each band was cut individually from the electrophoresis gel and destained completely. The antigens were obtained by harvesting the antigen bands from the gel by electroelution.

The antigens were then tested individually as ELISA antigens for their ability to detect and distinguish antisera to *M. gallisepticum* and *M. synoviae* in an enzyme-linked immunosorbent assay. The test sera was obtained from both laboratory induced infections and natural outbreaks of mycoplasmosis.

The *M. gallisepticum* antigens p64, p56, p26, and p24, which were selected on the basis of the criteria listed above, all performed well when tested as ELISA antigens. The ELISA test employing *M. gallisepticum* antigen p64 is superior to the presently available HI test (National Veterinary Services Lab, Ames, Iowa) in detecting antibodies early in the immune response and to atypical *M. gallisepticum* isolates. Furthermore, the p64 antigen was able to detect infection in all the natural field cases tested. Although the presently available *M. gallisepticum* SPA test detected antibodies three days before p64 in experimentally inoculated chickens, the p64 antigen was much less susceptible to false positive reactions. A combination of the *M. gallisepticum* antigens p26 and p24 was not able to detect infection in as many birds as the *M gallisepticum* p64 antigen or the HI test. However, this combination was able to detect infection in some birds that *M. gallisepticum* p64 could not. *M. gallisepticum* antigen p56 elicits a stronger response with *M. gallisepticum* antisera than p64. Both p56 and p26 detect *M. gallisepticum* infection relatively early in the infection. Turkeys experimentally infected with the S6 strain of *M. gallisepticum* responded strongly to p64 and p56 early in their immune response. However, they responded weakly or not at all to p26. Therefore, although p64 or p56 by itself is a superior ELISA antigen, a mixed antigen containing a combination of *M. gallisepticum* antigens p64, p56, p26, or p24 should constitute an optimally sensitive and specific antigen for an ELISA test.

The number of potential *M. synoviae* ELISA antigen candidates were less than for *M. gallisepticum;* none of the immunogenic proteins isolated from a *M. synoviae* isolate met all of the selection criteria outlined above. Of the three candidates that were chosen and purified, both p53 and p41 were in high quantities and both p41 and p22 appeared to be highly immunogenic. Although p53, which was isolated from a particular *M. synoviae* strain, could detect *M. synoviae* infection in the homologous situation, the antigen performed poorly when *M. synoviae* field sera was assayed. Furthermore, p41 shares a common epitope with an unidentified immunogenic protein of *M. gallisepticum.* However, *M. synoviae* p41 performed well with regard to sensitivity. *M. synoviae* p22 is sensitive to *M. synoviae* antisera, but did not elicit a response to antisera from birds in the early (first two weeks) stages of infection. Thus, a mixed antigen containing p41 and a more specific antigen such as p22 on an optimized plate ELISA should result in a more specific test. Furthermore, use of p41 or p22 as an *M. synoviae* ELISA antigen should greatly reduce, if not eliminate, the false positive results caused by the use of oil-emulsion vaccines in poultry.

Serum from chickens inoculated with commercial oil-emulsion vaccines were used to test the susceptibility of the purified antigens to false positive reactions correlated with such immunizations. All the purified antigens from both *M. gallisepticum* and *M. synoviae* performed well using these antisera.

Thus, *Mycoplasma gallisepticum* antigens p64, p56, p26, and p24 can be used either singly or in combination in an improved ELISA test for *Mycoplasma gallisepticum* infection in be used either singly or in combination in an improved ELISA test for *Mycoplasma synoviae* infection in poultry. Furthermore, these *Mycoplasma gallisepticum* and *Mycoplasma synoviae* tests can be combined in a diagnostic immunoassay kit to selectively and sensitively detect and distinguish infections in poultry caused by these two pathogenic mycoplasma species.

Furthermore, antisera to substantially purified antigens p64 and p41 were produced. The anti-p64 and anti-p41 sera reacted sensitively and specifically with proteins isolated from *M. gallisepticum* and *M. synoviae*, respectively. Thus, it may be possible to employ these antisera in immunoreactive tests, such as antigen capture assays, to detect *M. gallisepticum* or *M. synoviae* infection.

In an effort to facilitate the purification of these mycoplasma antigens, DNA from *M. gallisepticum* was inserted into *E. coli* to produce a set of clones that express *M. gallisepticum* antigens. Clones were screened immunologically with serum prepared from specific pathogen free leghorn chickens that had been infected with aerosolized *M. gallisepticum*. A single clone was chosen at random for comparison with a vector control by western immunoblot, revealing a polypeptide of 140 kD in the clone profile, but not the control profile, that reacted with the immune serum.

Accordingly, one of the objectives of this invention is to provide improved serological tests capable of the sensitive, selective, and early identification of *M. gallisepticum* and *M. synoviae* infection in poultry or infection caused by a combination of these two mycoplasmas. These serological tests exhibit a low incidence of false positive results. In addition, this invention provides a serological test for *M. gallisepticum* infection in poultry that is capable of sensitively and selectively detecting both serologically typical and atypical strains or isolates of *M. gallisepticum*.

A further object of this invention is to provide a diagnostic kit that employs a combination of serological tests for *M. gallisepticum* and *M. synoviae* and is capable of distinguishing *M. synoviae* infection from *M. gallisepticum* infection in poultry.

A still further object of this invention is to provide substantially purified *M. gallisepticum* or *M. synoviae* antigens that possess strong immunoreactivity with poultry antisera to the mycoplasma from which they were isolated but lack immunogenic cross-reactivity with poultry antisera to other mycoplasma species. Furthermore, this invention provides a process to isolate these antigens from *M. gallisepticum* or *M. synoviae*.

In addition, it is an object of this invention to provide antisera to these substantially purified antigens. This antisera can be used in appropriate immunoassays, such as antigen capture assays, to detect either *M. gallisepticum* or *M. synoviae* infection. Furthermore, it is an object of this invention to produce clones that express the antigenic portions of antigens that are specific to *M. gallisepticum* and *M. synoviae*. These and other objects and advantages of the present invention are apparent to persons skilled in the art from the following detailed description.

DETAILED DESCRIPTION OF THE INVENTION

Figure 1:
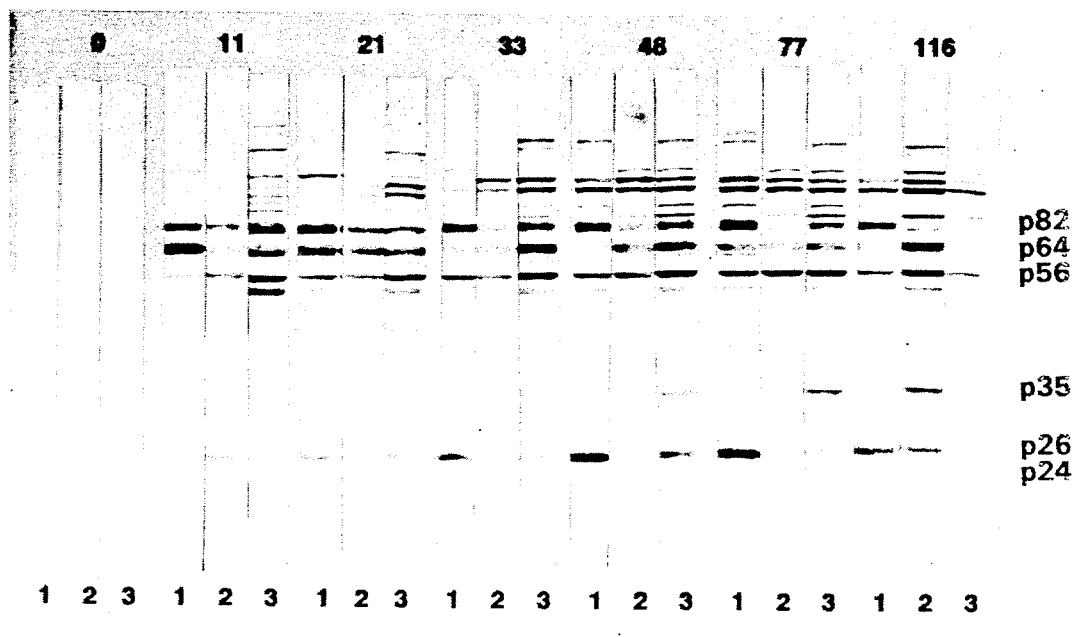
FIG. 1 shows immunoblots of cell proteins of *Mycoplasma gallisepticum* strain R with *Mycoplasma gallisepticum*-positive antisera collected over a period of 116 days from aerosol-inoculated chickens.

As used herein, the term "antigen" refers to a protein, polypeptide, or Coomassie blue staining band purified by the method described below and proteins or polypeptides which are substantially similar thereto, whether synthetic or naturally occurring. An antigen is said to be "substantially similar" to another antigen if it is capable of performing substantially the same function, and has substantially the same chemical structure. Thus, the term is intended to include synthesized proteins or polypeptides, proteins or polypetides purified from any stain or isolate within the species *M. gallisepticum* or *M. synoviae*, and proteins or polypeptides produced using recombinant technology. The term further includes proteins or polypeptides which are substantially the same as the naturally occurring protein or polypeptide but which differ therefrom by one or more amino acids while still having substantially the same antigenic activity.

The term "immunoassay" is intended to refer to a system for detecting the presence of particular immunoglobulins. Examples of immunoassays include, but are not limited to, enzyme-linked immunosorbant assays (ELISA), Western immunoblotting, agglutination, radioimmunoassays and immunodiffusion.

1. Identification of Species-Specific Immunoqenic Polypeptides

Western immunoblots of cell proteins of *M. gallisepticum* and *M. synoviae* with antisera to *M. synoviae* and *M. gallisepticum*, respectively, were examined to determine the extent of immunogenic cross-reactivity between these two mycoplasmas. A comparison between these immunoblots and those of the cell proteins of both mycoplasmas developed with their own antiserum revealed which protein bands were immunospecific to either *M. gallisepticum* or *M. synoviae*.

The R strain of *M. gallisepticum* and the F10-2AS isolate of *M. synoviae* were filter-cloned 3 times through a 450 nm filter and checked for purity by immunofluorescence. Cloned mycoplasmas were grown in Frey's medium with 12% swine serum (FMS) to log phase (until culture medium turned orange) at 37° C., then were collected and washed three times in 150 mM phosphate buffered saline solution (pH 7.2) by centrifugation at 10,000×g for 30 minutes at 4° C. Washed mycoplasma cells were solubilized in 10 mM Tris containing 0.2% (w/v) sodium deoxycholate, 0.1% (w/v) sodium dodecyl sulfate, 1.0% (v/v) Triton X-100, 10 mM EDTA, and 1 mM phenylmethylsulfonyl fluoride (pH 7.8) for 30 minutes at 37° C. and stored at −20° C. until used.

Solubilized mycoplasma proteins were assayed for protein content, mixed with lysis buffer consisting of 125 mM Tris, 4% (w/v) SDS, 10.0% (v/v) 2-beta mercaptoethanol, and 20 0% (v/v) glycerol, pH 6.8, and heated to 100° C. for 5 minutes. Samples (30 µg/well) were applied to 0.75 mm thick, 4% stacking/10% running SDS-PAGE gels and run overnight at 4 milliamps constant current/gel using the buffer system of Laemmli, Nature, 227:680–685 (1970).

Relative molecular weights of the proteins were estimated according to the procedure of Weber and Osborne, Biol. Chem., 244:4406 (1969) on SDS-PAGE 10% polyacrylamide gels (10% T, 2.7% C) using the buffer system of Laemmli, Nature, 227 680–685 (1970). Dalton Mark VII-L molecular weight markers (catalog # SDS-7, Sigma Chemical Co., St. Louis, Mo.) were employed for proteins less than approximately 70 kDa and Bio-Rad Low Molecular Weight Markers (catalog #161-0304, Richmond, Calif.) were employed for proteins greater than approximately 70 kDa.

The proteins were transferred to 0.45 µm nitrocellulose paper (Bio-Rad, Richmond, Calif.) at 50 volts constant voltage for 2 hours and total transferred protein was visualized using 0.1% amido black stain. Nitrocellulose strips with transferred mycoplasma proteins were blocked by incubation for 3 hours at room temperature in Tris buffered saline (TBS; 20 mM Tris, 500 mM NaCl, pH 7.5) containing 4 % calf serum. Primary antisera were diluted 1:80 in TBS containing 1% swine serum and 1% calf serum (TBS-sera). The diluted antisera were allowed to stand at room temperature for 15 minutes before incubating with nitrocellulose strips for 3 to 6 hours at room temperature and then overnight at 4° C. This was followed by four 8-minute washes in TBS containing 0.05% Tween 20. Affinity purified rabbit anti-chicken IgG (H+L chains)-horseradish peroxidase (Zymed Laboratories, South San Francisco, Calif.) was diluted 1:1000 in TBS-sera and incubated with nitrocellulose strips for 4 hours at room temperature. This was followed by 4 washes as above and then a 3-minute wash in TBS. Immunoblots were developed for 5 minutes using $H_2O_2$ and 4-chloro-1-napthol (Bio-Rad, Richmond, Calif.) as directed by the manufacturer.

The Western immunoblots of cell proteins from M. gallisepticum strain R with chicken antisera (diluted 1:80) to M. synoviae and M. gallisepticum obtained following both contact exposure and aerosol inoculation show that many epitopes are common to both M. gallisepticum and M. synoviae. However, comparison of the M. synoviae results with the M. gallisepticum results allow the identification of six M. gallisepticum immunogenic protein bands that lack cross-reactivity to M. synoviae: these bands have the estimated approximate relative molecular weights of 82 (p82), 63–65 (p64), 56 (p56), 35 (p35), 26 (p26), and 24 (p24) kDa.

Comparison of data from immunoblots of cell proteins of M. synoviae isolate F10-2AS with chicken antisera (diluted 1:80) to M. gallisepticum or M. synoviae obtained following both contact exposure and aerosol inoculation allows identification of two protein bands of M. synoviae with estimated relative molecular weights of 53–54 (p53) and 22 (p22) kDa that appear to be species specific. Also shown in the immunoblots is a highly immunogenic, but not species-specific, protein band having an estimated approximate relative molecular weight of 41 (p41) kDa. Six M. synoviae proteins were recognized by M. gallisepticum-positive serum showing fairly extensive cross-reaction between these two species.

2 Investigation of the Humoral Immune Response Over Time

The humoral immune response of white Leghorn chickens experimentally infected with M. gallisepticum or M. synoviae by either aerosol inoculation or contact exposure were examined over a period of time by immunoblotting. Specific-pathogen-free white Leghorn chickens were reared in Horsefall units and determined to be free of mycoplasma species prior to infection. At 8 weeks of age, 12 birds were moved to an isolation house with battery cages. Six of the birds were exposed using a nebulizer to a 5-minute aerosol inoculation with $10^9$ color changing units (CCU) per ml of viable M. gallisepticum strain R (22 medium passages) grown in Frey's medium with liposomes substituting for swine serum. Four hours later, 6 contact birds were introduced so that each of 2 cages contained three aerosol inoculated birds and three contact birds. In a second trial, ten white Leghorn chickens at 20 weeks of age were exposed to a 5-minute aerosol inoculation ($10^9$ CCU/ml) with M. synoviae isolate F10-2AS (13 medium passages) grown in Frey's medium with swine serum (FMS). Aerosol-inoculated chickens were caged individually in alternate cages in a layer cage battery system. Nine contact chickens were introduced four hours later and were caged individually adjacent to two aerosol-inoculated birds. Antisera were collected over time from each group. In both trials, uninoculated control birds were maintained in separate facilities.

At the end of the trials, all birds were examined by culture by swabbing the trachea for the presence of mycoplasma species and only the mycoplasma species used for inoculation was recovered. Contact birds were tracheal-cultured periodically to determine whether and approximately when contact infection occurred.

(a) M. gallisepticum results

Figure 2:
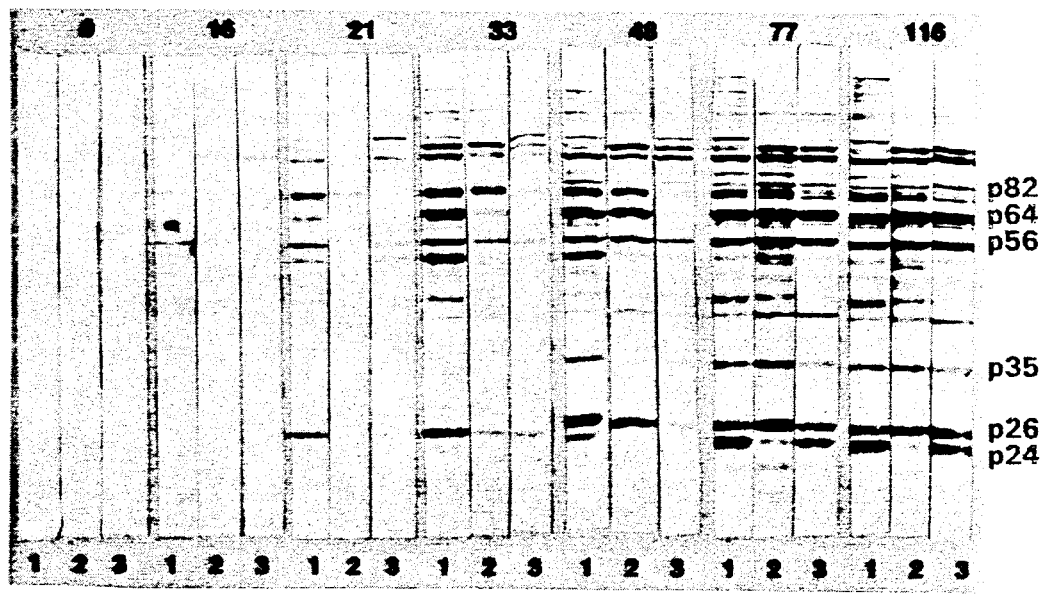
FIG. 2 shows immunoblots of cell proteins of *Mycoplasma gallisepticum* strain R with *Mycoplasma gallisepticum*-positive antisera collected over a period of 116 days from contact-exposed chickens.

Representative humoral immune responses of individual chickens to an aerosol inoculation and to contact exposure with M. gallisepticum are portrayed in FIG. 1 and FIG. 2, respectively. These figures show the immunoblots of cell proteins of M. gallisepticum strain R with M. gallisepticum -positive antiserum collected over time from the infected chickens. The bottom axis denotes the same three birds (1, 2, and 3) sampled at various days (top axis) post innoculation. All three aerosol-inoculated chickens produced a strong antibody response by day 11 that lasted throughout the 116-day trial. Although the response was delayed, the contact-exposed chickens responded as strongly to infection with M. gallisepticum as did the aerosol-inoculated birds (day 0 corresponded to the day the chickens were placed in contact with the aerosol-inoculated birds and M. gallisepticum contact-exposed chickens were negative by tracheal culture on day 6). M. gallisepticum was first isolated from birds one and three on day 11, and on day 16 from bird two. The protein bands p64, p56, and p26 were among the first to be recognized by chickens in both the aerosol and contact groups. Antisera from all M. gallisepticum infected birds reacted with p64, p56, and p26 and this response persisted throughout the trial. The occurrence of antibodies recognizing p82, p35, and p24 was more variable in individual birds with respect to onset and duration.

Figure 3:
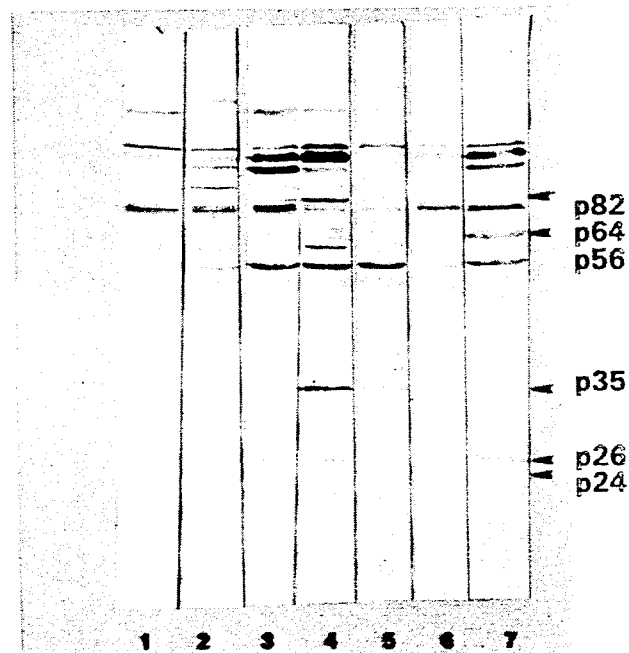
FIG. 3 shows immunoblots of cell proteins of *Mycoplasma gallisepticum* strain R with chicken antisera collected during natural field infections of *Mycoplasma gallisepticum*.

Antisera from chickens naturally infected with *M. gallisepticum* also were analyzed by immunoblotting as shown in FIG. 3. These chickens represented three separate outbreaks of *M. gallisepticum*; their antisera reacted with a number of antigens of *M. gallisepticum* strain R. The response to p64 varied and showed no correlation with HI titer. Two chickens (lanes 3 and 4) responded well to p64, three birds (lanes 1, 2, and 5) responded weakly to p64, and one bird (lane 6) showed no response to p64. Five chickens responded well to p56 (lanes 2-6). The response to other *M. gallisepticum* antigens varied among the chickens. However, all birds showed at least a weak response to p26.

(b) *M. synoviae* results

Figure 4:
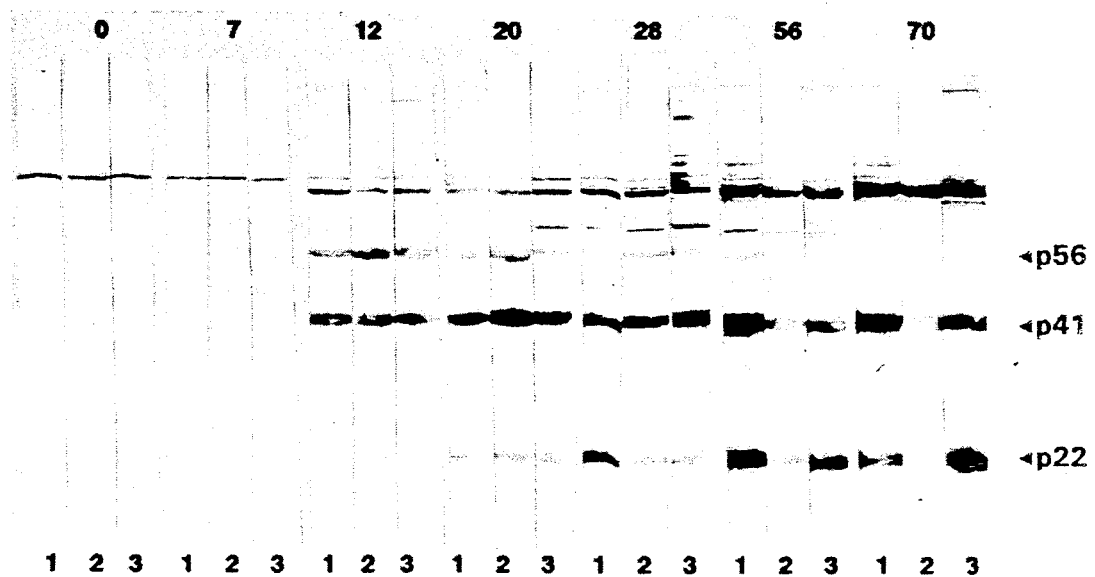
FIG. 4 shows immunoblots of cell proteins of *Mycoplasma synoviae* isolate F10-2AS with *Mycoplasma synoviae*-positive antisera collected over a period of 70 days from aerosol-inoculated chickens.
Figure 5:
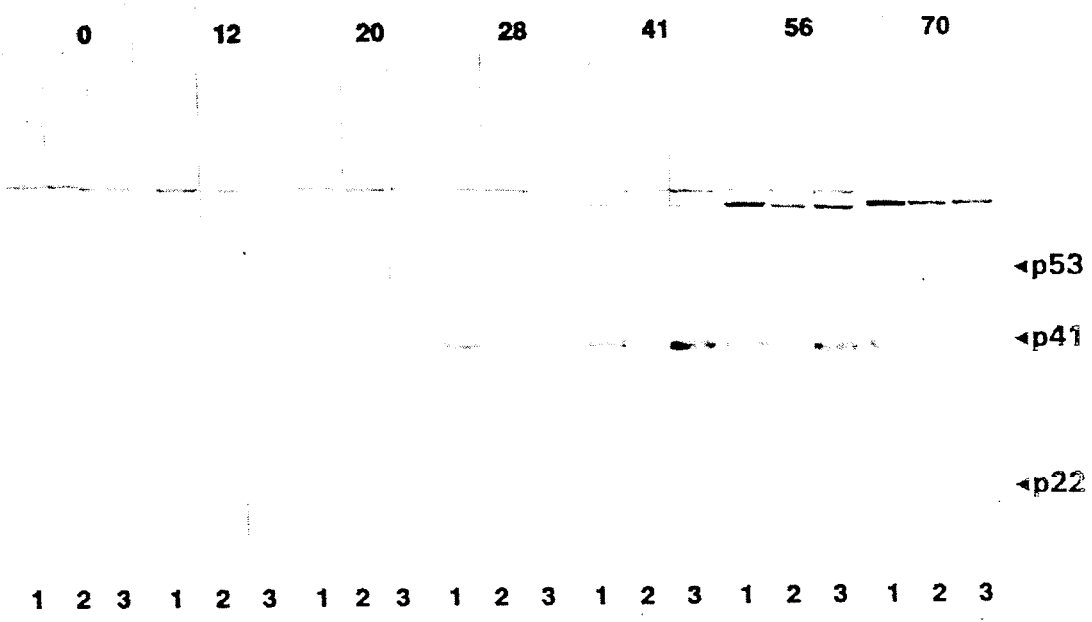
FIG. 5 shows immunoblots of cell proteins of *Mycoplasma synoviae* isolate F10-2AS with *Mycoplasma synoviae*-positive antisera collected over a period of 70 days from contact-exposed chickens.

Representative humoral immune responses of chickens to an aerosol inoculation or contact exposure to *M. synoviae* are shown in FIGS. 4 and 5, respectively. The bottom axis denotes the same three birds (1, 2, and 3) sampled at various days (top axis) post innoculation. Chickens infected by aerosolization of viable *M. synoviae* responded to more *M. synoviae* proteins and with greater intensity than did those birds infected by contact exposure. The aerosol-inoculated chickens responded to p53, p41, and p22 by day 12 and antibodies persisted until the end of the trial on day 70. *M. synoviae* contact-exposed chickens were negative by tracheal culture on day 6. *M. synoviae* was first isolated from birds one and two on day 10 and from bird three on day 14. Contact-exposed chickens responded to p53 and p41 as early as they did to any *M. synoviae* antigen. The response to p53 waned between day 28 and 56 in the aerosol inoculated birds. The response to p22 by *M. synoviae* contact-exposed chickens was approximately two weeks later than p53 and p41. *M. synoviae* protein bands of approximately 90 kDa were recognized on all immunoblots. This band does not indicate prior infection with any known mycoplasma because all chicken sera tested reacted with these protein bands.

Figure 6:
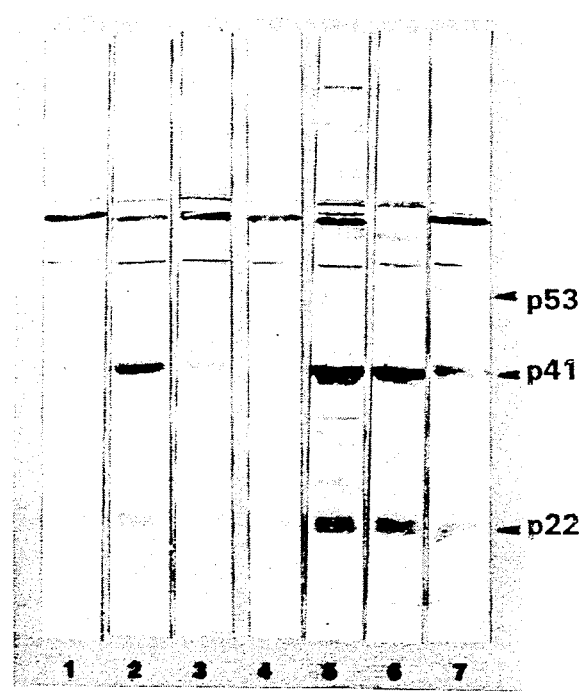
FIG. 6 shows immunoblots of cell proteins of *Mycoplasma synoviae* isolate F10-2AS with chicken antisera collected during natural field infections of *Mycoplasma synoviae*.

Antisera from chickens naturally infected with *M. synoviae* were analyzed by immunoblotting as shown in FIG. 6. These chickens represented four separate outbreaks of *M. synoviae* infection. All six chickens responded with varying intensity to p41 and p22. Only three chickens (lanes 1, 3, and 5) responded weakly to p53. There was no correlation of HI titer with the response to *M. synoviae* proteins as documented by immunoblotting.

3. Purification of Mycoplasma Antigens

Protein bands of *M. gallisepticum* and *M. synoviae* were purified in the following manner. SDS-PAGE gels (10%) with 22 lanes/gel were loaded with 60 μg protein/lane of either *M. gallisepticum* strain R or *M. synoviae* isolate F10-2AS. Electrophoresis occurred overnight at 8 milliamps constant current/gel. Gels were passively stained for 5 to 6 minutes in 0.2% Coomassie blue and then destained for 30 minutes in destaining solution (50% methanol, 10% glacial acetic acid, 40% distilled water). Gels were further destained in 25% methanol/75% distilled water until individual protein bands could be easily distinguished. Protein bands of interest were cut from gels with a razor blade and destained completely in destaining solution (8 to 20 hours). Antigen was electroeluted from the cut gels using a Model 422 electro-eluter (Bio-Rad, Rockville Centre, N.Y.) as instructed by the manufacturer. A 12,000 molecular weight cut off membrane was used for *M. gallisepticum* antigens p82, p64, p56, p35, p26/p24 (both bands cut and eluted together) and *M. synoviae* antigens p53, p41 and p22; a 3,500 molecular weight cut off membrane was used to purify *M. gallisepticum* antigen p26 (separately from p24) and *M. synoviae* antigen p22. Eluted proteins were stored at −80° C. until used.

Preparative SDS-PAGE was an adequate method to purify these protein bands for use as antigens. SDS-PAGE gels of the purified bands stained with Coomassie blue revealed that relatively large amounts of each of the protein bands could be harvested from SDS-PAGE gels. Immunoblots of the purified antigens showed that antisera to *M. gallisepticum* reacted with purified p82, p64, p56, p35, p26, and p24 but not with *M. synoviae* purified antigens p53 and p22. Antisera to *M. synoviae* reacted with immunoblots of *M. synoviae* purified antigens p53, p41, and p22 but with none of the *M. gallisepticum* purified antigens.

4. Reactions of Antiserum to p64 and p41 with Mycoplasma Isolates

Antisera to p64 and p41 was prepared by collecting sera from specific-pathogen-free (SPF) chickens immunized with purified p64 and p41, respectively. The antigens for immunization were purified by cutting the antigen band from SDS-PAGE gels followed by electroelution (as described above). The p64 antigen used for immunization was twice purified in this manner. The antigen in solution was emulsified with Freund's complete adjuvant or an incomplete oil adjuvant in a ratio of one part antigen solution to 3 parts adjuvant. Three-week-old SPF chickens received 1 ml intramuscularly and 1 ml subcutaneously of either antigen in Freund's complete adjuvant in the initial immunization. At five weeks of age the chickens received a booster immunization identical to the initial immunization, except that the antigens were in an incomplete adjuvant. Blood was collected 10 days after the booster.

Western immunoblots of this antisera with proteins isolated (as described above) from various mycoplasma isolates were developed to ascertain the reactivity of the antisera with different mycoplasma strains and isolates and with mycoplasma species other than *M. gallisecticum* or *M. synoviae*.

Antisera to p64 strongly reacted with a protein band having a molecular weight of approximately 64 kDa isolated from *M. gallisepticum* strains R, PG31, S6, A5969, and F; with *M. gallisepticum* atypical strains 703, 503, and 730; and other *M. gallisepticum* isolates from chickens, turkeys, a peacock, and a parrot. Antisera to p64 did not react with protein bands isolated from the avian mycoplasma *M. synoviae* (except for a nonspecific *M. synoviae* band that reacts with negative antisera also), *M. gallinaceum*, *M. gallinarum*, *M. pullorum*, *M. meleaguidis*, or *M. iowae*. This antisera also did not react with avian Acholeplasma, but did react with the human pathogen, *M. pneumoniae*.

Antisera to p41 reacted with protein bands isolated from *M. synoviae* isolates found in chickens located in Texas, Ohio, Georgia, North Carolina, Arkansas, and Brazil. Although all of the isolates reacted with the p41 antisera, the molecular weight of the reacting protein varied from isolate to isolate. Antisera to p41 did not react with protein bands isolated from the avian mycoplasma *M. gallisepticum*, *M. gallinarum*, *M. gallinaceum*, *M. pullorum*, or *M. meleaguidis* or the closely related Acholeclasma. However, Antisera to p41 reacted weakly with an approximately 41 kDa protein band from *M. iowae*, which is usually found in turkeys.

Because both anti-p64 and anti-p41 sera are sensitive and specific to antigens isolated from *M. gallisepticum* and *M. synoviae*, respectively, they might be suitable for use in antigen capture assays. For instance, anti-p64 serum can be bound to a ELISA plate and a certain volume of a culture of *M. gallisepticum* could be added so that the antiserum binds the organism. Rabbit antisera to *M. gallisepticum* can then be added followed by addition of antisera to rabbit IgG conjugated to an enzyme to allow the detection of the *M. gallisepticum* antigen. Because at least part of the p64 band is a membrane protein, it is likely that the anti-p64 serum can interact with the p64 molecule(s) allowing capture of the intact *M. gallisecticum* cells.

5. Evaluation of Purified Mycoplasma Protein Bands as ELISA Antigens

Antisera from chickens infected with *M. gallisepticum* (experimental inoculations and natural infections), *M. synoviae* (experimental inoculation and natural infections), *M. gallinarum*, or immunized with oil-emulsion vaccines were used to test the purified antigens described above in a dot-ELISA system. The dot-ELISA results were compared with those obtained using laboratory-prepared and commercial SPA tests and laboratory-prepared HI tests.

(a) Dot-ELISA protocol

Purified mycoplasma antigens as described above were slightly diluted with a KOH solution to increase the ability of the antigen to bind to nitrocellulose paper; the final concentration of KOH in the antigen preparations was 1% (v/v). Antigen in 1% KOH were applied to 0.2 μm gridded nitrocellulose paper (Micro Filtration Systems, Dublin, Calif.) in 2.0 to 3.0 μl dots with a micro-pipette. The applied antigens were allowed to dry for 2 hours at room temperature. After drying the antigen dots, the nitrocellulose paper was washed for 5 minutes in Tris buffered saline (TBS; 20 mM Tris, 500 mM NaCl, pH 7.5). Blocking of sites unoccupied by antigen dots was accomplished by incubating the nitrocellulose paper at 4° C. overnight in TBS containing 4% calf serum. Primary antisera were diluted 1:50 in TBS containing 1% calf serum/1% swine serum/1% Frey's medium. Nitrocellulose paper with antigen dots were cut into strips so that each strip had up to 5 different antigen dots. This allowed the testing of many different antigens with one antiserum dilution. Nitrocellulose strips were incubated with the primary antisera (2 ml volumes) for 75 minutes at room temperature in an incubation tray (Hoefer Scientific Instruments, San Francisco, Calif.) placed on a rocker platform. Next, the nitrocellulose strips were washed 4 times for 5 minutes each with TBS containing 0.05% Tween 20 (TBS-T20). Affinity purified rabbit anti-chicken IgG (H+L chains)-horseradish peroxidase (Zymed Laboratories, South San Francisco, Calif.) was diluted 1:1000 in TBS containing 1% calf serum and 1% swine serum. This anti-chicken IgG conjugate was incubated with the nitrocellulose strips for 75 minutes at room temperature as for primary antisera. The nitrocellulose strips were washed three times in TBS-T20 and one final time in TBS. Nitrocellulose strips were developed by incubation for 5 minutes in a solution containing $H_2O_2$ and 4-chloro-1-napthol (Bio-Rad) as directed by the manufacturer.

(b) Antisera production

Twenty-six specific-pathogen-free (SPF) Leghorn chickens were maintained in Horsefall units until inoculated. Ten SPF chickens at 8 weeks of age (Group 1) were moved into cages in an isolation house and inoculated with *M. gallisepticum* strain R (16 medium passages) grown in Frey's medium with 12% swine serum (FMS). Each bird in group 1 received 2 drops (approximately 70 μl) intraocularly and 1 drop (approximately 35 μl) intranasally. Just prior to inoculation, the viable *M. gallisepticum* inoculum was diluted 1:10 using sterile phosphate buffered saline solution (PBS), pH 7.2. The *M. gallisepticum* inoculum was titrated by 10-fold serial dilutions in FMS broth just after bird inoculation and was found to have a titer of $10^8$ color changing units (CCU)/ml. Thus, each bird in Group 1 received approximately $10^7$ CCU of viable *M. gallisepticum.*

Ten SPF chickens at 9 weeks of age (Group 2) were moved into cages in a separate isolation house. Group 2 birds were inoculated with viable *M. synoviae* isolate F10-2AS (20 medium passages) grown in FMS. Each bird in Group 2 received 3 drops of 1:10 dilution of a viable *M. synoviae* suspension as described above for the *M. gallisepticum* inoculated birds. This inoculum was titrated just after chicken inoculation and each bird received approximately $10^7$ CCU of viable *M. synoviae.*

The remaining 6 SPF chickens at 8 weeks of age (Group 3) were sham infected with 3 drops of sterile 1:10 diluted FMS as described above for *M. gallisepticum* inoculated birds. Group 3 birds were maintained in Horsefall units throughout the trial. All birds were determined to be free of mycoplasma species before inoculation. Serum was collected during the trial from all birds in each group.

Antisera from chickens two to four weeks post inoculation with a commercial bursal disease virus vaccine, commercial fowl coryza vaccine (*Haemophilus paragallinarum*), or inactivated *Staphylococcus aureus*-in-oil were produced, as described in Ahmad et al., *Avian Dis.*, 32:519–526 (1988). These antisera were used to test the susceptibility of the purified dot-ELISA antigens to false positive reactions caused by the use of oil-emulsion vaccines in poultry.

Highly cross-reactive chicken antisera to *M. gallisepticum* strain R and *M. synoviae* isolate F10-2AS produced by aerosol inoculations were used to test the specificity of the purified *M. gallisepticum antigens* p64, p56, p26/24, and p26 and *M. synoviae* antigens p41 and p22 in a dot-ELISA. Many of these antisera were found to be cross-reactive in the commercial *M. gallisepticum* SPA and ELISA tests and Western immunoblotting. Many of the *M. gallisepticum* antisera were found to be cross-reactive in the commercial *M. synoviae* SPA test and Western immunoblotting.

Antisera to 12 *M. gallisepticum* isolates were produced by intra-air sac inoculation of broiler-type chickens with one of the 12 isolates as described in Kleven et al., *Avian Dis.* 34:731–741 (1988). Antiserum from these *M. gallisepticum*-inoculated birds was collected 4 weeks after inoculation.

Chicken antisera from suspected natural field outbreaks of mycoplasmosis on commercial farms were stored at −20 ° C. until they were assayed with the purified dot-ELISA antigens. Most of the flocks were cultured from the trachea for the presence of mycoplasmas. If mycoplasmas were isolated, they were identified by a direct fluorescent antibody technique using antiserum produced in rabbits to individual avian mycoplasma species.

(c) SPA and HI tests

*M. gallisepticum* and *M. synoviae* laboratory-prepared SPA antigens were prepared and used as described in Glisson et al, *Avian Dis.* 28:397–405 (1984). *M. gallisepticum* and *M. synoviae* commercial SPA antigen (Intervet America, Millsboro, Del.) were used in accordance with the manufacturer's instructions. Agglutinations were scored on a 0 to 4 scale with scores of 2 or higher considered positive. The HI tests for *M. gallisepticum* and *M. synoviae* were performed with four hemagglutination units in a microtiter system as described by Vardaman et al. *Poult. Sci.* 49:157–157 (1970). HI titers of 1:40 were considered positive. SPA and HI antigens were prepared from *M. gallisepticum* strain A5969 and *M. synoviae* strain WVU 1853.

(d) Results

Figure 7:
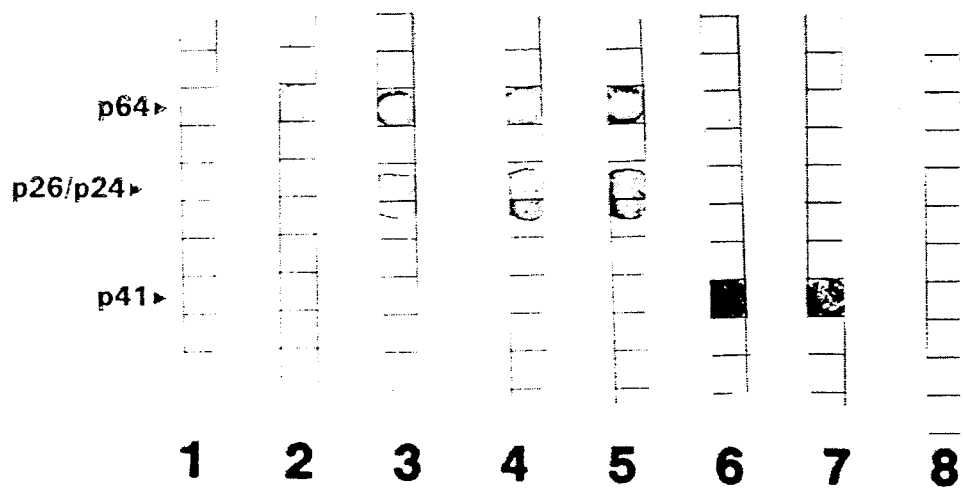
FIG. 7 shows a dot-ELISA that employs *Mycoplasma gallisepticum* antigens p64 and p26/p24 and *Mycoplasma synoviae* antigen p41 to test chicken antisera to *Mycoplasma gallisepticum*, *Mycoplasma synoviae*, and *Mycoplasma gallinarum*.

FIG. 7 shows typical positive and negative dot-ELISA results. Lanes 1–5 show the response of antisera from one aerosol-inoculated *M. gallisepticum* strain R infected bird to *M. gallisepticum* antigens p64 and p26/p24 over time (6, 11, 21, 33 and 99 days post innoculation, respectively) and lanes 6 and 7 show the response of antisera from a chicken aerosol inoculated with *M. synoviae* isolate F10-2AS to *M. synoviae* antigen p41 (41 and 28 days, respectively). Lane 8 shows the response of antiserum from a chicken naturally infected with *M. gallinarum*. The *M. gallisepticum* antigen p64 elicited a humoral response before p26/p24; the *M. gallisepticum* -positive antisera did not react with the *M. synoviae* antigen p41. Conversely, lanes 6 and 7 show a positive reaction between *M. synoviae* -positive antisera and the *M. synoviae* antigen p41 and a negative reaction between this antisera and the *M. gallisepticum* antigens p64 and p26/p24. None of these mycoplama antigens reacted positively with the *M. gallinarum*-positive antisera.

Thus, the *M. gallisepticum* antigens p64, p56, p26, and p24 and the *M. synoviae* antigens p41 and p22 may be incororated individually or in combinations into an immunoassay, such as an ELISA. These immunoassays, packaged either singly or in combination, may constitute a diagnostic kit. These kits can be designed to allow detection of only *M. gallisepticum* , only *M. synoviae*, or both *M. gallisepticum* and *M. synoviae* infection in poultry.

TABLE 1

Ability of the *M. gallisepticum* (MG) serum plate agglutination (SPA) test, MG hemagglutination-inhibition (HI) test, and purified MG dot-ELISA antigens p64 and p26/24 to detect seroconversion in MG-inoculated chickens (Group 1).[A]

Number of sera positive/number sera tested

| Days Post Inocul. | PDRC[B] MG SPA | INTER[B] MG SPA | MG HI | MG dot-ELISA[C] p64 | MG dot-ELISA[C] p26/24 |
|---|---|---|---|---|---|
| 0 | 0/10 | 0/10 | 0/10 | 0/10 | 0/10 |
| 6 | 1/10 | 2/10 | 0/10 | 0/10 | 0/10 |
| 7 | 2/10 | 6/10 | 0/10 | 0/10 | 0/10 |
| 9 | 9/9 | 8/9 | 0/9 | 7/9 | 3/9 |
| 12 | 10/10 | 10/10 | 0/10 | 10/10 | 5/10 |

TABLE 1-continued

Ability of the *M. gallisepticum* (MG) serum plate agglutination (SPA) test, MG hemagglutination-inhibition (HI) test, and purified MG dot-ELISA antigens p64 and p26/24 to detect seroconversion in MG-inoculated chickens (Group 1).[A]

Number of sera positive/number sera tested

| Days Post Inocul. | PDRC[B] MG SPA | INTER[B] MG SPA | MG HI | MG dot-ELISA[C] p64 | MG dot-ELISA[C] p26/24 |
|---|---|---|---|---|---|
| 16 | 10/10 | 10/10 | 5/10[D] | 10/10 | 5/10 |

[A]Chickens were inoculated intraocularly and intranasally with approximately $10^7$ color changing units of MG strain R. One serum gelled on day 9 post inoculation and could not be assayed.
[B]PDRC — laboratory-prepared MG SPA; INTER — commercially prepared (Intervet) MG SPA.
[C]p64 — approximately 64 kilodalton (kDa) antigen from MG strain R; p26/24 — approximately 26 and 24 kDa antigens from MG strain R. Both antigens were purified from SDS-PAGE gels.
[D]All positive HI titers were 1:40.

Table 1 shows the ability of *M. gallisepticum* purified antigen p64 and p26/p24 to detect seroconversion in chickens inoculated with viable *M. gallisepticum* (Group 1) compared to *M. gallisepticum* SPA tests and the *M. gallisepticum* HI test. The laboratory-prepared and commercial SPA tests detected antibodies first on the sixth day after inoculation. Both purified *M. gallisepticum* antigens detected antibodies first on day 9. None of the day 12 serum samples were positive when tested by HI. However, by day 16, 5 of 10 birds tested positive with 1:40 HI titers. No positive reaction were seen with Group 1 antisera when *M. synoviae* purified antigens p53, p41, and p22 were evaluated using the dot-ELISA protocol.

TABLE 2

Ability of the *M. synoviae* (MS) serum plate agglutination (SPA) test, MS Hemagglutination-inhibition (HI) test, and purified MS dot-ELISA antigens p53 and p41 to detect seroconversion in MS-inoculated chickens (Group 2).[A]

Number sera positive/number sera tested

| Days Post Inocul. | PDRC[B] MS SPA | INTER[B] MS SPA | MS HI | MS dot-ELISA[C] p53 | MS dot-ELISA[C] p41 |
|---|---|---|---|---|---|
| 0 | 0/10 | 0/10 | 0/10 | 0/10 | 0/10 |
| 6 | 5/10 | 0/10 | 0/10 | 0/10 | 0/10 |
| 7 | 8/10 | 1/10 | 0/10 | 0/10 | 0/10 |
| 9 | 10/10 | 4/10 | 0/10 | 4/10 | 0/10 |
| 11 | 10/10 | 5/10 | 0/10 | 7/10 | 5/10 |
| 15 | 10/10 | 9/10 | 0/10 | 9/10 | 7/10 |

[A]Chickens were inoculated intraocularly and intranasally with approximately $10^7$ color changing units of MS isolate F10-2AS.
[B]PDRC — laboratory-prepared MS SPA; INTER — commercially prepared (Intervet) MS SPA.
[C]p53 — approximately 53 kDa antigen from MS isolate F10-2AS; P41 — approximately 41 kDa antigen from MS isolate F10-2AS. Both antigens were purified from SDS-PAGE gels.

Table 2 shows the ability of *M. synoviae* purified antigens p53 and p41 to detect seroconversion in chickens inoculated with viable *M. synoviae* (Group 2) compared with *M. synoviae* SPA tests and the *M. synoviae* HI test. The laboratory-prepared SPA antigen detected seroconversion in 5 of 10 birds on day 6 post inoculation. The commercial *M. synoviae* SPA antigen detected antibodies first on day 7 in 1 of 10 birds. *M. synoviae* purified antigens p53 and p41 first detected antibodies on day 9 and day 11, respectively. The HI test uniformly gave negative titers on days 15 and 22 (antisera from birds in Group 2 were tested by HI on day 22, but not with purified antigens). *M. synoviae* purified antigen p22 (purified using the 12,000 MW cut off membrane) and *M. gallisepticum* purified antigen p64 and p26/p24 yielded no positive reactions when testing antisera from Group 2 chickens.

Antisera from sham inoculated control birds (Group 3) were tested using all five purified antigens. These antisera produced no positive reactions with the two *M. gallisepticum* purified antigens p64 or p26/p24 or with the three *M. synoviae* purified antigens p53, p41, or p22 in the dot-ELISA.

TABLE 3

Ability of the MG and MS purified antigens to react in a dot-ELISA with chicken antisera produced to 12 MG isolates.[A]

| Antisera to MG Isolate | MG HI[B] Titer | Number sera positive/number sera tested | | |
|---|---|---|---|---|
| | | MG ELISA[C] antigen p64 | MG ELISA[C] antigen p26/24 | MS ELISA[C] antigen p41 |
| K781 (R) | ≧1:40 | 4/5 | 1/5 | 0/5 |
| K810 (F) | ≦1:20 | 2/2 | 0/2 | 0/2 |
|  | ≧1:40 | 3/3 | 0/3 | 0/3 |
| K2221 (383T) | ≦1:20 | 1/2 | 0/2 | 0/2 |
|  | ≧1:40 | 3/3 | 1/3 | 1/3 |
| K1486 | ≧1:40 | 5/5 | 4/5 | 3/5 |
| K1659 | ≦1:20 | 2/2 | 0/2 | 0/2 |
|  | ≧1:40 | 3/3 | 1/3 | 0/3 |
| K1501 | ≦1:20 | 4/5 | 0/5 | 0/5 |
| K1453 | ≦1:20 | 3/3 | 0/3 | 0/3 |
|  | ≧1:40 | 2/2 | 1/2 | 0/2 |
| K2221 (236C) | ≦1:20 | 2/2 | 0/2 | 0/2 |
|  | ≧1:40 | 3/3 | 0/3 | 0/3 |
| K1503 | ≦1:20 | 3/5 | 2/5 | 0/5 |
| K2221 (309C) | ≦1:20 | 1/1 | 0/1 | 0/1 |
|  | ≧1:40 | 4/4 | 1/4 | 0/4 |
| K503[D] | ≦1:20 | 4/13 | 0/13 | 0/13 |
| K703[D] | ≦1:20 | 4/19 | 0/19 | 0/19 |

[A]Antisera were collected from chickens 4 weeks post intra-airsac inoculation.
[B]Four hemagglutinating units of MG stain A5969 used HI antigen.
[C]p64 — approximately 64 kilodalton (kDa) antigen from MG strain R; p26/24 — approximately 26 and 24 kDa antigens from MG strain R; p41 — approximately 41 kDa antigen from MS isolate F10-2AS. All three antigens were purified from SDS-PAGE gels.
[D]K503 and K703 are considered atypical serological variants of MG.

Table 3 shows the ability of purified *M. gallisepticum* dot-ELISA antigen p64 and p26/p24 and *M. synoviae* dot-ELISA antigen p41 to detect antibodies in serum from birds infected with one of 12 *M. gallisepticum* isolates compared with the *M. gallisepticum* HI test (using strain A5969 as HI antigen). Antigen p64 yielded more positive reactions than the HI test when testing these antisera. Antisera to three isolate (K1501, K503, and K703) were uniformly negative using the HI test. However, *M. gallisepticum* antigen p64 detected antibodies in some samples in each of these three groups. Some birds in groups inoculated with one of 7 of the 12 *M. gallisepticum* isolates responded with antibodies that reacted with *M. gallisepticum* antigen p26/p24. Two serum samples that were negative using *M. gallisepticum* antigen p64 were positive using p26/p24. In 2 cases, *M. gallisepticum*-positive antisera reacted with *M. synoviae* dot-ELISA antigen p41.

TABLE 4

Ability of MG and MS purified antigens to react in a dot-ELISA with chicken antisera from natural field outbreaks of mycoplasmosis.[A]

| Case | Mycoplasma[B] Isolated | SPA[C] Pos | HI[C] Pos | Diag-[D] nosis | Number sera pos./number sera tested | | | |
|---|---|---|---|---|---|---|---|---|
| | | | | | MG ELISA[E] | | MS ELISA[E] | |
| | | | | | p64 | p26/24 | p53 | p41 |
| 89-1009 | N/A[F] | N/A | N/A | MS | MS | 0/4 | 0/4 | N/A | 2/4 |
| 89-1015 | N/A | N/A | N/A | MS | MS | 0/4 | 0/4 | 1/4 | 3/4 |
| 89-1013 | N/A | N/A | N/A | MS | MS | 0/5 | 0/5 | 0/5 | 1/5 |
| K2847 | N/A | N/A | N/A | MS | MS | 0/7 | 0/7 | N/A | 3/7 |
| 89-1056 | B,D,MG | MG,MS | MG | MG | 5/13 | 3/13 | 0/10 | 0/13 |
| 89-1200 | B,D,MG | MG,MS | MG | MG | 5/12 | 2/12 | 0/8 | 0/12 |
| K2786 | MG | MG | MG | MG | 3/4 | 2/4 | 0/4 | 0/4 |
| K2833BC | MG | MG,MS | MG | MG | 8/12 | 5/12 | 0/4 | 1/12 |
| K2818D | B,D | MG,MS | MG | MG | 5/5 | 0/5 | 0/5 | 0/5 |
| K2846 | B | None | None | B | 0/5 | 0/5 | N/A | 0/5 |
| K2848 | B | None | None | B | 0/5 | 0/5 | N/A | 0/5 |

[A]Antisera and in some cases tracheal cultures were submitted to our laboratory for mycoplasma diagnosis.
[B]B:*M. gallinarum;* D:*M. gallinaceum.* Mycoplasmas isolated identified by a fluorescent antibody technique.
[C]Serum plate agglutination (SPA) and hemagglutination-inhibition (HI) antigen for MG and MS were made from strains A5969 and WVU1953, respectively. HI titers of ≧1:40 were positive.
[D]Final diagnosis based on serology and culture results available.
[E]p64 — approximately 64 kilodalton (kDa) antigen from MG strain R; p26/24 — approximately 26 and 24 kDa antigens from MG strain R; p53 — approximately 53 kDa antigen from MS isolate F10-2AS; p41 — approximately 41 kDa antigen from MS isolate F10-2AS. All four antigens were purified from SDS-PAGE gels.
[F]N/A — Not applicable; either serology or culturing was not done.

Table 4 shows the ability of *M. gallisepticum* purified antigens p64 and p26/p24 and *M. synoviae* purified antigens p53 and p41 to detect antibodies in sera from chickens in flocks experiencing a natural outbreak of mycoplasmosis. *M. gallisepticum* antigen p64 detected antibodies in sera from birds in each case diagnosed as *M. gallisepticum* infection. *M. gallisepticum* antigen p26/p24 detected antibodies in sera from birds in 4 of 5 cases in which *M. gallisepticum* was diagnosed. Three birds were positive when using *M. gallisepticum* antigen p26/p24 but negative with *M. gallisepticum* antigen p64.

*M. synoviae* antigen p41 detected antibodies in sera from birds in each case in which the final diagnosis was *M. synoviae* infection (Table 4). However, *M. synoviae* antigen p41 detected antibodies in one case in which *M. synoviae* was not diagnosed. *M. synoviae* antigen p53 only detected antibodies in one of nine birds in which *M. synoviae* was diagnosed. In two cases, no serological evidence of *M. gallisepticum* or *M. synoviae* infection was found using the SPA test, HI test, and purified antigens. *M. gallinarum* was isolated from these serologically negative flocks.

Antisera from birds 2 and 4 weeks post inoculation with a commercial bursal disease virus vaccine, commercial fowl coryza vaccine (*Haemophilus paragallinarum*), or inactivated *Staphylococcus aureus*-in-oil were tested with *M. gallisepticum* p64 and p26/24 and *M. synoviae* p53, p41, and p22 antigens in a dot-ELISA. Of 60 serum samples, 59 tested negative with these five purified antigens. One sample from a bird inoculated with IBV vaccine reacted weakly with *M. gallisepticum* antigen p64.

Five *M. synoviae*- and twelve *M. gallisepticum*-positive antisera samples produced by aerosol inoculation of chickens and known to be highly cross-reactive were used to test the specificity of *M. gallisepticum* antigens p64, p56, p26/p24 and p26 and *M. synoviae* antigens p41 and p22. The 5 antisera to *M. synoviae* did not react with *M. gallisepticum* antigens p64 or p56. Three of the *M. synoviae* -positive antisera reacted weakly with *M. gallisepticum* antigen p26/p24. The 12 *M. gallisepticum* -positive antisera did not react with *M. synoviae* antigens p41 or p22. However, the *M. gallisepticum*-positive sera did react with the *M. gallisepticum* purified antigens and the *M. synoviae*-positive sera reacted with the *M. synoviae* purified antigens.

Thus, the use of purified antigens from *M. gallisepticum* and *M. synoviae* can be used to increase the reliability of serological diagnosis of these two pathogenic avian mycoplasmas. *M. gallisepticum* antigen p64 was more sensitive than the *M. gallisepticum* HI test in detecting seroconversion in experimentally infected birds and in detecting antibodies to some of the 12 *M. gallisepticum* isolates tested. Furthermore, *M. gallisepticum* antigen p64 was able to detect antibodies to serologically atypical *M. gallisepticum* isolates K503 and K703. HI tests using *M. gallisepticum* strains A5969, S6, or R as antigen were uniformly negative when testing the serum from K503 and K703 inoculated chickens.

In addition, *M. gallisepticum* antigen p64 was able to detect *M. gallisepticum* antibodies in chicken sera from natural outbreaks of *M. gallisepticum* in the 5 cases in which *M. gallisepticum* was diagnosed. *M. gallisepticum* antigen p26/p24 did not detect antibodies in as many birds or to as many isolates as antigen p64. However, 5 serum samples that were negative using *M. gallisepticum* antigen p64 were positive using *M. gallisepticum* antigen p26/p24. Thus, a combination of *M. gallisepticum* antigen p64 and p26/p24 may be useful in the design of an ELISA for antibodies to *M. gallisepticum* .

*M. synoviae* antigen p41 was superior to the HI test in detecting seroconversion to *M. synoviae* in experimentally infected chickens. In naturally infected chickens, p41 detected antibodies in serum from the 4 cases diagnosed as *M. synoviae*. However, antigen p41 has been shown to share epitopes with an unidentified *M. gallisepticum* antigen. One positive reaction using a *M. gallisepticum*-positive-*M. synoviae*-negative field serum was seen using *M. synoviae* antigen p41. Although not species-specific, antigen p41 may still be used to improve *M. synoviae* serology because of the elimination of false positives correlated with the use of oil-emulsion vaccines in poultry.

*M. synoviae* antigen p22 yielded no positive reactions with any antisera tested. However, it appears to be quite immunogenic in chickens experimentally infected or naturally infected with *M. synoviae* . Amido black staining revealed that 3 μl dots of p22 on nitrocellulose paper strips contained very little protein. The small molecular weight of p22 may have allowed much of the antigen to pass through the 12,000 MW cut-off membrane during the electroelution process. More recently, a second batch of *M. synoviae* p22 has been purified using a 3,500 MW cut-off membrane. When using this smaller MW cut-off membrane, enough p22 was collected to use as 2 μl dots in the dot-ELISA.

Using the 3,500 MW cut-off membrane during purification, the purified *M. synoviae* antigen p22 was tested using *M. gallisepticum* -positive chicken antisera and *M. synoviae*-positive chicken antisera in the dot-ELISA. The p22 antigen was sensitive with the *M. synoviae* antisera; however, antisera from birds in the first two weeks of infection did not respond. One of the *M. gallisepticum* -positive antisera tested reacted weakly with p22. Whether this weak reaction was a true cross-reaction is not known.

Purified *M. gallisepticum* antigens p26 and p56 were also tested using *M. gallisepticum* -positive chicken antisera and *M. synoviae*-positive chicken antisera in a dot-ELISA. Both these antigens were sensitive and specific and detected *M. gallisepticum* infection relatively early in infection. None of the tested *M. synoviae*-positive antisera reacted with either the p26 antigen or the p56 antigen.

6. Method of Producing Clones that Express Mycoplasma Antigens

(a) Procedure

*M. gallisepticum* strain A5969 was cultured in Frey's medium containing 12% swine serum. E. coli strain Y1090 was grown in LB broth containing 50 μg/ml ampicillin and 0.2% maltose. Soft agar overlays were plated on LB agar also containing ampicillin at 50 μg/ml. Growth temperatures were 37° C. except as indicated.

*M. gallisepticum* DNA was extracted as described in Krause et al., Inf. & Imm., 47:157-165 (1985) and sheared by passage through a 25 gauge needle approximately 2500 times. DNA in the size range of 5 to 7 kilobasepairs was purified by sucrose gradient centrifugation and prepared for cloning as described by Young et al., *Proc. Natl. Acad. Sci. USA* 82:2583 (1985), with the exception that a NACS column (Bethesda Research Laboratories, Gaithersburg, Md.) was used to remove excess linkers. *M. gallisepticum* DNA was ligated with Eco RI-digested and dephosphorylated lambda-gt11 DNA (Promega Corp., Madison, Wisc.) and packaged using Packagene preparations (Promega). Recombinant phage preparations were used to infect *E. coli* Y1090 grown to late logarithmic phase as described above, harvested by centrifugation, and suspended in 0.4 volume of 10 mM $MgSO_4$. Following a 20 min. incubation at room temperature, the phage-bacteria suspension was mixed with LB soft agar, pour-plated onto LB agar plates containing ampicillin, and incubated at 42° C. overnight.

Phage-infected *E. coli* Y1090 were plated in LB soft agar and incubated for 5 hours at 42° C. Nitrocellulose disks previously saturated with 10 mM IPTG to induce lac-directed expression of cloned genes by recombinant lambda-gt11, were placed on the surface of the soft agar and the incubation continued overnight at 37° C. The filters, now bound by proteins present in the plaques formed by the recombinant phage, were removed and placed for seven hours in blocking buffer [TBS(20 mM Tris—0.5 M NaCl, pH 7.5)]containing 4% powdered milk to occupy any remaining protein-binding sites on the nitrocellulose.

The primary antiserum for clone bank screening was prepared from specific pathogen free chickens infected with *M. gallisepticum* strain A5969 by aerosol. The serum was preadsorbed with an *E. coli* lysate to reduce the background reactivity to host determinants in the plaque lifts and was used at a dilution of 1:10,000 in TBS containing 2% calf serum. Plaque lifts were incubated overnight at 4° C. in the primary antiserum with gentle mixing, washed four times with TBS containing 0.5% Tween 20 (TTBS) and transferred to TBS-calf serum containing affinity purified rabbit anti-chicken IgG (H and L chains) conjugated with alkaline phosphatase (Jackson Immunoresearch Laboratories, Inc., West Grove, Pa.) at a 1:5000 dilution. After a four hour incubation at room temperature, the filters were washed as above and developed with NBT-BCIP substrate (Fisher Scientific, Pittsburgh, Pa.) for alkaline phosphatase.

Clones reacting positively were picked with sterile pasteur pipettes to SM buffer containing a drop of chloroform. Approximate titers were established for each, and clones were subsequently screened by plating each to near confluency on LB agar containing ampicillin in individual wells of 24-well culture dishes (Costar, Cambridge, Mass.), with IPTG present at 10 mM in the LB soft agar overlay. Following a 4.5 hour incubation at 42° C. for plaque formation, the recombinant phage proteins were harvested by overlaying the plaques with lambda dilution buffer at room temperature for 1.5-2 hours with gentle mixing and transferring each supernatant to individual wells of a 96-well vacuum manifold. The phage proteins were collected onto nitrocellulose in the manifold and subsequently screened for antigen expression as described.

E. coli-absorbed anti-M. gallisepticum serum was evaluated by western immunoblot. Bacterial cultures were prepared as described above, collected by centrifugation, washed, and suspended in sample buffer for sodium dodecylsulfate-polyacrylamide gel electrophoresis (SDS-PAGE). A single positive clone and a vector control were also compared by western immunoblot. Phage proteins, collected from plaque eluates as described above, were mixed with an equal volume of supersaturated ammonium sulfate (76% w/vol, pH 7.5-8.0) and incubated overnight on ice to precipitate the proteins. The precipitates were recovered by centrifugation (20 min. at 10,000×g at 4° C.), washed twice with phosphate-buffered saline, pH 7.2, resuspended in sample buffer for SDS-PAGE, and heated at 68° C. for 10 minutes. Proteins were separated by SDS-PAGE according to Laemmli, Nature 227:680 (1970), and transferred electrophoretically to nitrocellulose. Western blots were probed with antisera as described above for plaque lifts.

(b) Results

Many mollicutes prefer to use the otherwise generally universal termination codon UGA as a codon for tryptophan. This becomes a problem when the expression of cloned mollicute genes in E. coli is attempted. Premature termination of translation is likely to occur because E. coli are not appropriately equipped with a tRNA specific for UGA. The expression vector lambda-gt11 was chosen for the potential formation of fusion polypeptides when passenger DNA is inserted into the lacZ gene of lambda-gt11 in the proper orientation and reading frame. This circumvents to some degree the problems associated with UGA termination. When a polyclonal serum having reactivity with multiple epitopes on the proteins of interest is used to screen clone banks, the probability of identifying positive clones improves.

Although serum collected from standard white leghorn chickens infected by aerosol inoculation of M. gallisepticum reacted with numerous M. gallisepticum proteins, as determined by SDS-PAGE and western immunoblot, there was also a very strong reaction with a number of E. coli determinants, even after serial dilution of the serum and extensive absorption with E. coli lysates. Such high antibody titers to E. coli would make it impossible to distinguish between clones expressing M. gallisepticum antigens and antigen-negative clones. To circumvent this problem, sera from M. gallisepticum aerosol-infected, specific pathogen free white leghorns was used. While a certain level of reactivity to E. coli determinants was observed in such sera, it is possible to minimize this reactivity by dilution of the serum and absorption with E. coli lysates without an apparent loss of reactivity to M. gallisepticum protein antigens.

The lambda-gt11 clone bank consisted of $1.65 \times 10^5$ phage, approximately 75% of which were identified as recombinants by the insertional inactivation of the $\beta$-galactosidase gene of the vector. When plaques were screened for expression of M. gallisepticum antigens, approximately 250, or less than 1% of the clones, yielded the purple ring around the periphery of the plaque on the nitrocellulose filters, as is characteristic of antigen-positive clones.

The positive clones were collected individually and stored for further analysis. To facilitate comparisons between clones the screening protocol was modified as described above, such that the protein lysates generated from phage plaques were collected in buffer and transferred to nitrocellulose using a vacuum manifold. This made it possible to compare numerous clones with different sera on a larger scale. No reactivity was observed in the normal serum to plaque proteins from any clone or the vector control. Likewise, the vector control failed to react with the anti-M. gallisepticum serum. Variability was observed in the reactivity of the anti-M. gallisepticum serum to 22 clones, though the reactivity for any given clone was consistent from one screening to the next. A few clones failed to yield a positive signal when retested in this manner. Because any clone yielding even a weak signal was collected following the original screening, it is possible that a few might have been false-positives, accounting for their failure to react positively in the secondary screening. The variability from one clone to the next was not surprising and could be a function of the level of antigen expression in E. coli, differences in antibody titers to various epitopes, stability of the cloned DNA or gene product in E. coli, or other possible alternatives.

A single clone was selected randomly for comparison with the vector control by SDS-PAGE and western immunoblot.

Comparison of proteins detected by anti-M. gallisepticum serum in the vector lysate and clone lysate reveal prominent polypeptide of approximately 140 kilodaltons in the clone profile but not in the control profiles. The polypeptide's size is indicative of a possible fusion polypeptide with $\beta$-galactosidase.

What is claimed is:

1. A purified Mycobacterium gallisepticum antigen having the characteristics of ATCC No. 40748 of a molecular weight of abut 56,000 and substantially lacking immunogenic cross reactivity with Mycoplasma synoviae.

* * * * *